United States Patent [19]

Heuvelmans et al.

[11] Patent Number: 5,035,246
[45] Date of Patent: Jul. 30, 1991

[54] METHOD FOR CARRYING OUT HEMODYNAMIC MEASUREMENTS ON A PATIENT AND FLOW-DIRECTED BALLOON CATHETER USED FOR THIS

[76] Inventors: Joannes H. A. Heuvelmans, Leiduinstraat 4/2, 1058 SJ Amsterdam; Hieltje Goslinga, Voorstraat 17, 3633 BB Vreeland, both of Netherlands

[21] Appl. No.: 213,694

[22] Filed: Jun. 30, 1988

[30] Foreign Application Priority Data

Jun. 30, 1987 [NL] Netherlands .................. 8701536

[51] Int. Cl.$^5$ .................................. A61B 5/02
[52] U.S. Cl. ...................................... 128/673
[58] Field of Search ............... 128/672-675, 128/691-692, 713, 344; 604/96; 606/191, 192, 198

[56] References Cited

U.S. PATENT DOCUMENTS

| 3,995,623 | 12/1976 | Blake et al. | |
|---|---|---|---|
| 4,502,488 | 3/1985 | Degironimo et al. | 128/713 X |
| 4,508,103 | 4/1985 | Calisi | 128/673 |
| 4,543,961 | 10/1985 | Brown | |
| 4,601,706 | 7/1986 | Aillon | 128/673 X |
| 4,610,256 | 9/1986 | Wallace | 128/673 X |
| 4,621,646 | 11/1986 | Bryant | 128/692 |
| 4,637,401 | 1/1987 | Johnston | 128/713 X |
| 4,733,669 | 3/1968 | Segal | 128/663 |
| 4,777,951 | 10/1988 | Cribier et al. | 128/344 |
| 4,815,472 | 3/1989 | Wise et al. | 128/748 X |
| 4,856,529 | 8/1989 | Segal | 128/673 |

OTHER PUBLICATIONS

Physiologic Signal Acquisition and Processing for Human Hemodynamic Research in a Clnical Cardiac-Catheterization Laboratory—see p. 697.
Catheter for Intravascular Measurement of Blood Flow: Technical Details—p. 277, 5-1977.
Simultaneous Measurement of Pulmonary Artery and Pulmonary Artery Occlusion Pressure, by H. Goslinga et al., Blood Viscosity and Circulatory Filling Pressure in Clinical Practice, pp. 37–46, 1990 (article).
A New on Concept of the Circulation or the Importance of Blood Viscosity and Circulatory Filling Pressure, by Viggo-Spectramed, 1990 (brochure).

Primary Examiner—Ruth S. Smith
Assistant Examiner—J. P. Lacyk
Attorney, Agent, or Firm—Bachman & LaPointe

[57] ABSTRACT

A method for carrying out hemodynamic measurements on a patient, using a low-directed balloon catheter, which is connected to a measuring unit and is at least provided with a distal measuring lumen and a balloon-inflating lumen, comprising the steps of inserting the catheter by way of a suitable vein and further by way of the right atrium and ventricle into the pulmonary artery until the distal end with the inflated balloon in wedge position is stuck in a branch thereof and closes off the latter. A proximal measuring lumen is provided a few centimeters apart from the distal measuring lumen. Then the pulmonary arterial pressure (PAP) is measured, as long as the catheter has not yet arrived in the wedge position, via both the proximal and distal measuring lumina and the two relevant, virtually identical pressure curves are simultaneously recorded.

In the wedge position of the catheter with the balloon inflated, the pulmonary arterial pressure (PAP) and the pulmonary capillary wedge pressure (PCWP) via both said measuring lumina are measured respectively.

A flow-directed balloon catheter for hemodynamic measurements for use with the above method, said catheter being provided with a distal measuring lumen, a balloon-inflating lumen, and a proximal measuring lumen a few centimeters apart from the distal measuring lumen.

8 Claims, 9 Drawing Sheets

METHOD FOR CARRYING OUT HEMODYNAMIC MEASUREMENTS ON A PATIENT AND FLOW-DIRECTED BALLOON CATHETER USED FOR THIS

BACKGROUND OF THE INVENTION

The invention relates to a method for carrying out hemodynamic measurements on a patient, using a flow-directed balloon catheter, which is connected to a control and pressure-measuring unit and is at least provided with a distal measuring lumen and a balloon-inflating lumen, comprising the steps of inserting the catheter by way of a suitable vein until the distal end is positioned inside the thorax, and of subsequently inflating the balloon and of inserting the catheter further by way of the right atrium and ventricle into the pulmonary artery until the distal end with the balloon in wedge position is stuck in a branch thereof and closes off the latter. By measuring lumen, the opening end of a through tube is meant, which tube is connected at the other end to the control and pressure-measuring unit.

This method and the catheter used for this are known, inter alia, from the article "Hemodynamic Monitoring" by N. Buchbinder and W. Ganz in "Anesthesiology", Aug. 1976, vol 45, no. 2, pages 146-155.

In this known method and catheter, a number of hemodynamic measurements are carried out in order to gain an impression therewith of the functioning of heart and circulation. The pulmonary arterial pressure (PA pressure) and the pulmonary capillary wedge pressure (PCW pressure) play a very important role here. The pulmonary capillary wedge pressure is regarded as being a good measure of the end-diastolic pressure in the left ventricle because there is a continuous head of fluid (blood) between the left atrium and the catheter end in wedge position. As a result the PCW pressure can be designated as the filling pressure in the left atrium. The functioning of the left ventricle as a pump is determined to a considerable extent by the end-diastolic volume in the left ventricle. For a satisfactory approximation of this volume, the end-diastolic pressure in this left ventricle can be used. Catherization of an artery would be necessary to measure this pressure directly. Instead of this, the PCW pressure, which can be assessed by routine measurement with hemodynamic monitors, is used. It is evident that a partial or unsatisfactorily controlled wedge position of the catheter makes the measurement unreliable. A partial wedge position will generally be recognized by the pressure curve shown on a monitor. However, this is not always the case because PCW pressure curves often do not show the "ideal picture" and, because there is great variability in PCW pressure curves.

Additionally, the known method of carrying out hemodynamic measurements has the problem that the PA pressure is measured during introduction of the catheter with the inflated balloon into the pulmonary artery and that the PCW pressure is measured at a subsequent instant when the wedge position of the catheter is reached. It also holds that the PA pressure is measured when the catheter has been brought into position without the balloon being inflated and that the PCW pressure is measured at a subsequent instant, after inflating the balloon. Due to the fact that these curves are recorded only at consecutive instants in this way they can therefore be assessed and evaluated on the monitor exclusively with consideration of the time difference. A further problem which occurs is that a catheter with non-inflated balloon may come in a wedge position which is displaced upwards, which may not be noticed or is not directly noticeable because the PCW pressure curve cannot always satisfactorily be distinguished from the PA pressure curve which is measured first. Such an upward displaced wedge position, which may be caused with a non-inflated balloon by some artefact or other, may have very adverse effects on the blood through-flow in the pulmonary artery of the patient.

SUMMARY OF THE INVENTION

The invention aims at overcoming the above-mentioned problems and at providing an exceptionally efficient and safe method and a catheter used for this, by which is the safety of insertion and positioning of the catheter and the quality and control of the pulmonary pressure measurement are guaranteed.

This is achieved, according to the invention, in a method of the type mentioned at the outset in a manner such that a proximal measuring lumen is provided in the catheter a few centimeters apart from the distal measuring lumen, and that during the insertion of the catheter into the pulmonary artery, as long as the catheter has not yet arrived in the wedge position, the pulmonary arterial pressure is measured both via the proximal measuring lumen and via the distal measuring lumen and that the two relevant pressure curves which are virtually identical are simultaneously recorded by the measuring unit and/or represented thereon.

In a further embodiment of the method according to the invention, the method comprises the step of subsequently measuring, in the wedge position of the catheter with the balloon inflated, the pulmonary arterial pressure and the pulmonary capillary wedge pressure via the proximal measuring lumen and via the distal measuring lumen respectively and of simultaneously recording the two relevant, mutually different pressure curves with the measuring unit and/or representing them thereon. By this means, the moment at which the catheter arrives in the wedge position can be clearly detected by the two said curves diverging, as a result of which the simultaneous measurement of PA pressure and PCW pressure relative to each other is independent of interfering cardiac and respiratory influences.

In another embodiment of the method according to the invention, the method comprises the step of incidentally inflating the balloon in the wedge position of the catheter, the pressures measured simultaneously via the two measuring lumina in the uninflated and inflated state of the ballon producing pressure curves, which are virtually identical and mutually different, respectively, on the measuring unit as a result of which the wedge position is exactly determined and a reliable measurement of the two said pressures is guaranteed. Thereafter, in a spontaneously assumed and upward-displaced wedge position of the catheter with the balloon uninflated, the pulmonary arterial pressure and pulmonary capillary wedge pressure measured simultaneously via the proximal measuring lumen and via the distal measuring lumen will produce different pressure curves on the measuring unit as a result of which the moment at which the catheter arrives spontaneously in an upward-displaced wedge position with the balloon uninflated can be clearly detected by the divergence of the two said curves and an alarm can be given.

In yet another embodiment of the method according to the invention, the method comprises the step of measuring, during the insertion of the catheter by way of the right atrium and ventricle into the pulmonary artery or during removal of the catheter therefrom, the pressure on one side and on the other side of the tricuspid valve and/or the pulmonary valve, by means of the proximal and distal measuring lumina, so that the pressure gradient over the said valve(s) is recorded and/or represented on the measuring unit by means of two pressure curves.

The flow-directed balloon catheter mentioned in the outset is designed for carrying out the abovementioned methods in a manner such that a proximal measuring lumen is provided a few centimeters apart from the distal measuring lumen which makes it possible to measure the pulmonary arterial pressure and the pulmonary capillary wedge pressure simultaneously in the wedge position of the catheter. Present catheter may also be implemented such that each measuring lumen includes a pressure transducer, f.i. in chip form. Said transducer directly converts the pressure, measured at said lumen, into an electrical signal. Said signal is transmitted to the measuring unit instead that the pressure, otherwise present in the lumen and corresponding tube, is converted into a signal via a transducer in the measuring unit per se.

It is known in practice to provide such a flow-directed balloon catheter with a proximal lumen for measuring pressures, this being provided, however, at a distance of 25 to 30 cm from the distal tip. This proximal lumen is solely intended for measuring the right artrial pressure or the central venous pressure when the distal tip of the catheter is located in the pulmonary artery. Furthermore, particular fluids for infusion or medicines may be administered via this lumen.

BRIEF DESCRIPTION OF THE DRAWINGS

The invention will be explained in detail by means of an embodiment with reference to the drawings, in which.

DETAILED DESCRIPTION

Figure 1:
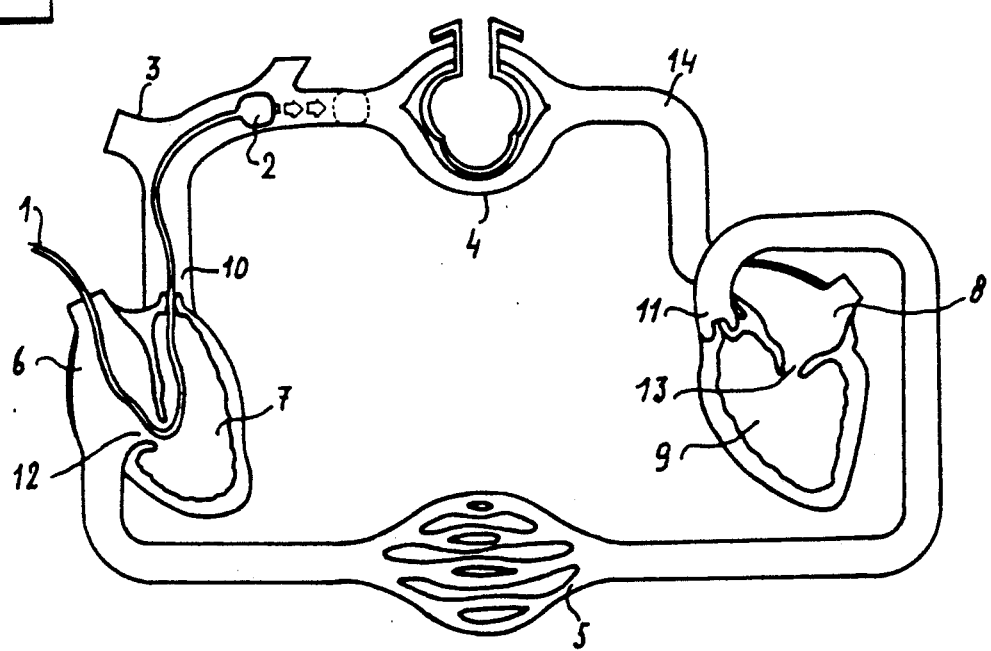
FIG. 1 shows a simplified diagram of the systemic blood circulation in human beings.

FIG. 1 shows diagrammatically the systemic blood circulation with the heart in diastole, i.e. with the ventricles 7 and 9 relaxed, the pulmonary valve 10 and aortic valve 11 closed and the tricuspid valve 12 and mitral valve 13 opened. In this, 1 designates a catheter inserted into the pulmonary artery 3. Part of the pulmonary circulation, the systemic circulation of the body, the right atrium, the right ventricle, the left atrium, the left ventricle and the pulmonary vein are indicated diagrammatically by 4, 5, 6, 7, 8, 9 and 14, respectively. It can be seen how the flow-directed balloon catheter 1 with the balloon 2 inflated has arrived near the wedge position in the pulmonary artery 3.

Figure 2:
FIG. 2 shows a view of a known flow-directed balloon catheter.
Figure 3:
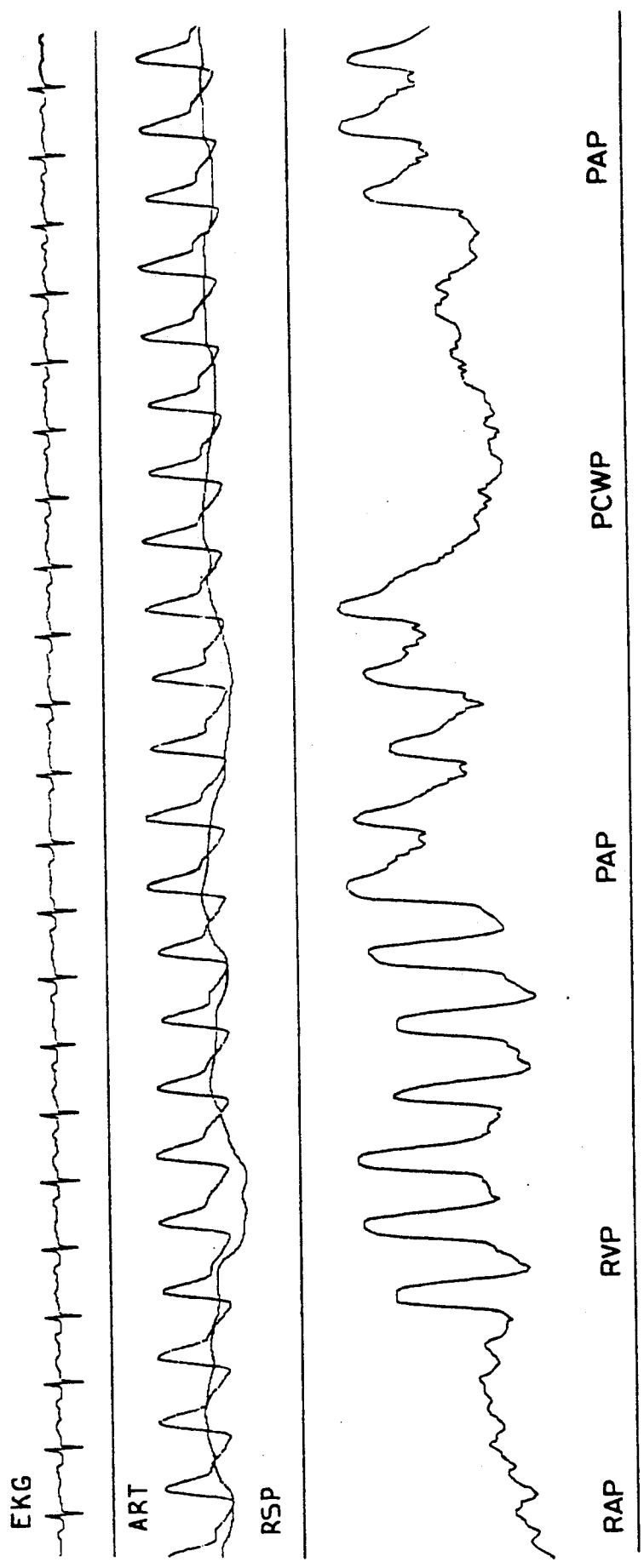
FIG. 3 shows a curve exemplifying the blood pressure measured via the catheter from the right atrium to the wedge position.

FIG. 2 shows a known catheter provided with a distal measuring lumen 15, a balloon-inflating lumen 16 and a thermistor 17 (the function of which is explained hereinafter). During insertion of the catheter the distal measuring lumen can be used to measure the pressure consecutively in the right atrium, right ventricle and thereafter in the pulmonary artery as is shown in FIG. 3. This figure shows at the bottom specifically, viewed from the left, in succession the right atrium pressure (RAP), right ventricular pressure (RVP), pulmonary arterial pressure (PAP) and pulmonary capillary wedge pressure (PCWP) during insertion of the catheter and the pulmonary arterial pressure (PAP) again during removal of the catheter or deflation of the balloon. This figure furthermore shows the electrocardiogram (EKG), the radial arterial pressure (ART) and respiration (RSP) of said patient.

Figure 4:
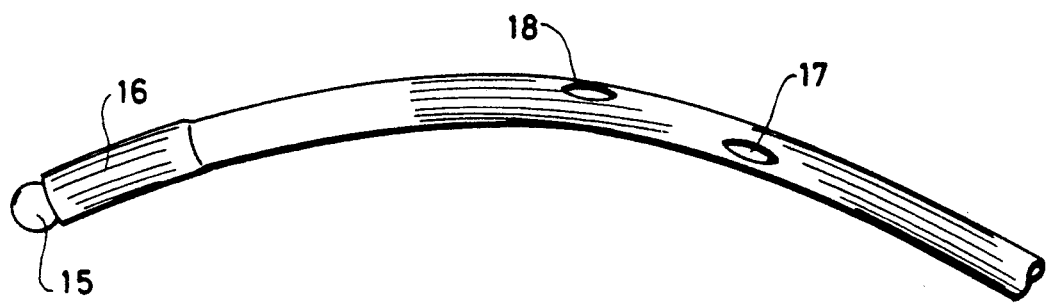
FIG. 4 shows a view of the flow-directed catheter according to the invention.

FIG. 4 shows the catheter according to the invention which is additionally provided with a proximal measuring lumen 18 a few centimeters apart from the distal measuring lumen 15. As indicated before each lumen may include a pressure (chip) transducer. This embodiment makes it possible to measure simultaneosly the PA pressure and PCW pressure and the pressures at either side of the triscuspid valve and on either side of the pulmonary valve as indicated by FIGS. 5 to 8.

As mentioned before, the position of the distal end of the catheter may represent a possible risk for the patient. In fact, the catheter may spontaneously move into an upward-displaced wedge position with the balloon uninflated. As a result, the blood supply to the region of the lung located behind this is shut off, and the consequence may be a pulmonary infarct. Such an unexpected displacement of the catheter tip without inflated balloon into an upward-displaced wedge position is not always noticed or it is not always directed recognisable from the PA pressure curve or the PCW pressure curve which then occurs. However, in this situation the new catheter can contribute to an alarm being given by the control and pressure measuring unit.

Figure 5:
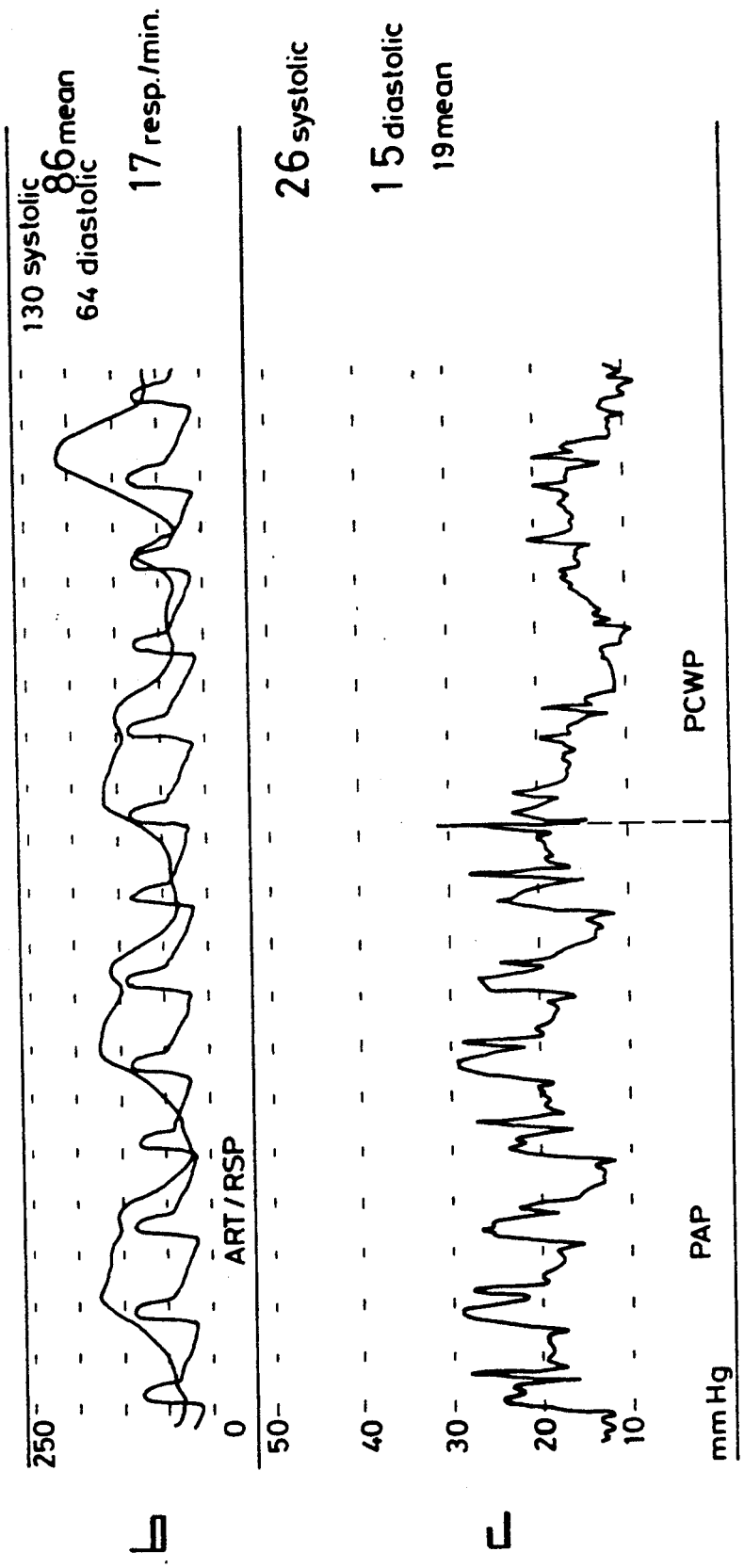
FIG. 5 shows curves of the pulmonary arterial pressure and the pulmonary capillary wedge pressure measured according to the state of the art and of some other parameters.

FIG. 5 consecutively shows the electrocardiogram (FIG. 5a), the radial arterial pressure (ART) and respiration (RSP) of a patient (FIG. 5a), and the pressure measured in the pulmonary artery (FIG. 5c) in mm Hg. This PA pressure measured with the known catheter passes over to the PCW pressure during further insertion of the catheter with inflated balloon or when the catheter is already in the wedge position after inflation of the balloon. CVP and TMP means control venous pressure and temperature respectively.

Figure 6:
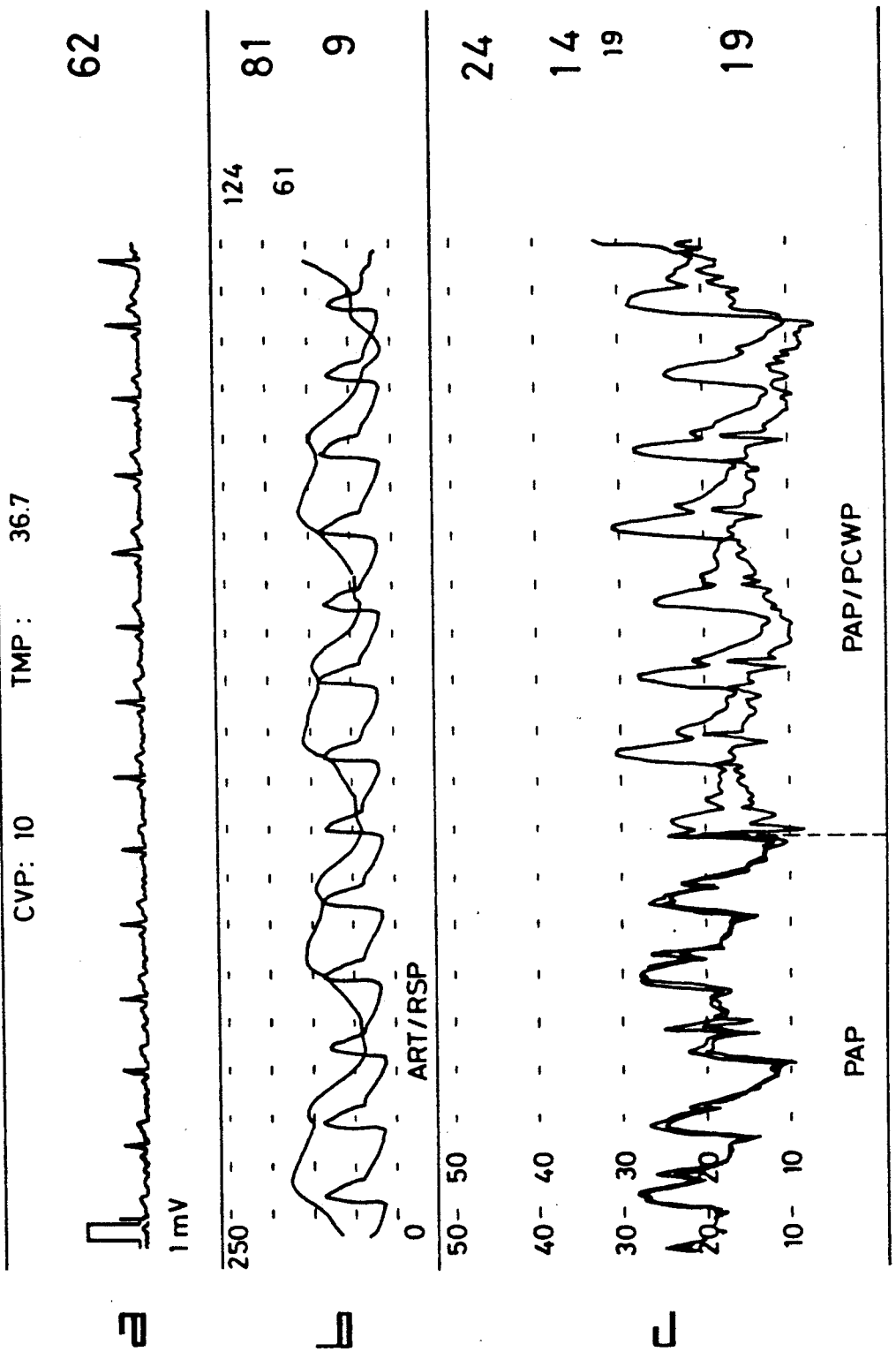
FIG. 6 shows curves of the pulmonary arterial pressure and the pulmonary capillary wedge pressure measured according to the invention, and of some other parameters.

FIG. 6 consecutively shows the electrocardiogram (FIG. 6a), the radial arterial pressure (ART) and respiration (RSP) of a patient (FIG. 6b), and the pressures measured by the distal and proximal measuring lumina of the catheter according to the invention (FIG. 6c) in the pulmonary artery. During further insertion of the catheter with the balloon inflated or when the catheter is already in the wedge position after inflation of the balloon, the two curves will diverge because the distal measuring lumen will measure the PCW pressure and the proximal measuring lumen will measure the PA pressure.

Due to the fact that the PA and PCW pressure curves can be measured simultaneously, control of the pulmonary pressure measurement is considerably improved. When the catheter is in position, but not in the wedge (balloon not inflated), the PA pressure curve and the PCW pressure curve converge. If this is not the case the catheter has come spontaneously in an upward-displaced wedge position or the two pressure systems are no longer exactly synchronous (artefact transducer, incorrect calibration procedure, etc.). In the case of a signel pulmonary pressure curve it will not be possible to detect these deviations as quickly.

Figure 7:
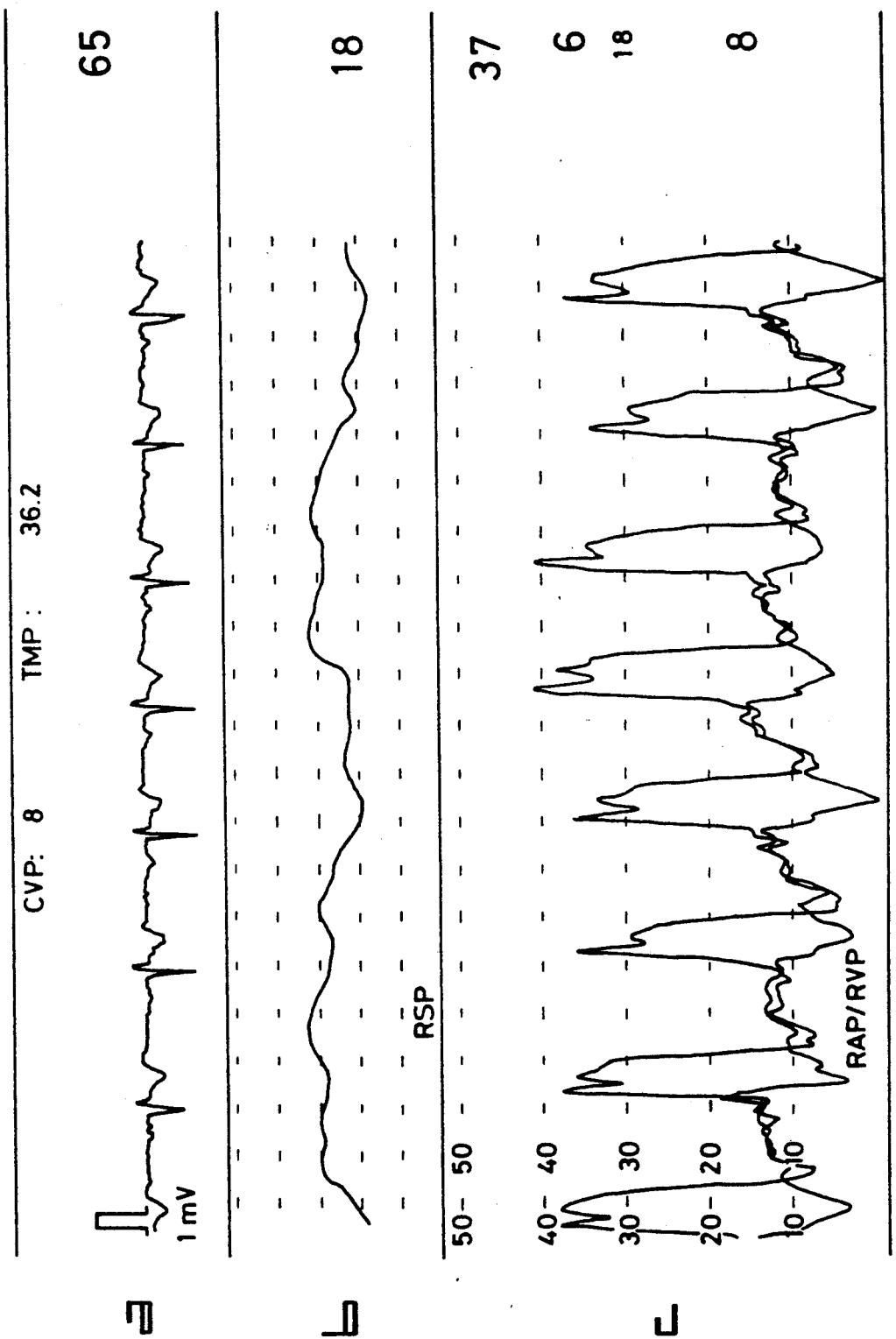
FIGS. 7 and 8 show curves of the pressures measured according to the invention on either side, of the tricuspid valve and the pulmonary valve, and some other parameters.

FIG. 7 consecutively shows for a patient: the electrocardiogram (FIG. 7a), the respiration (FIG. 7b) and the simultaneously measured right atrial pressure (RAP: bottom curve) and right ventricular pressure (RVP: top curve) (FIG. 7c). The two curves in FIG. 7c are measured by the proximal measuring lumen and distal measuring lumen of the catheter according to the invention.

Figure 8:
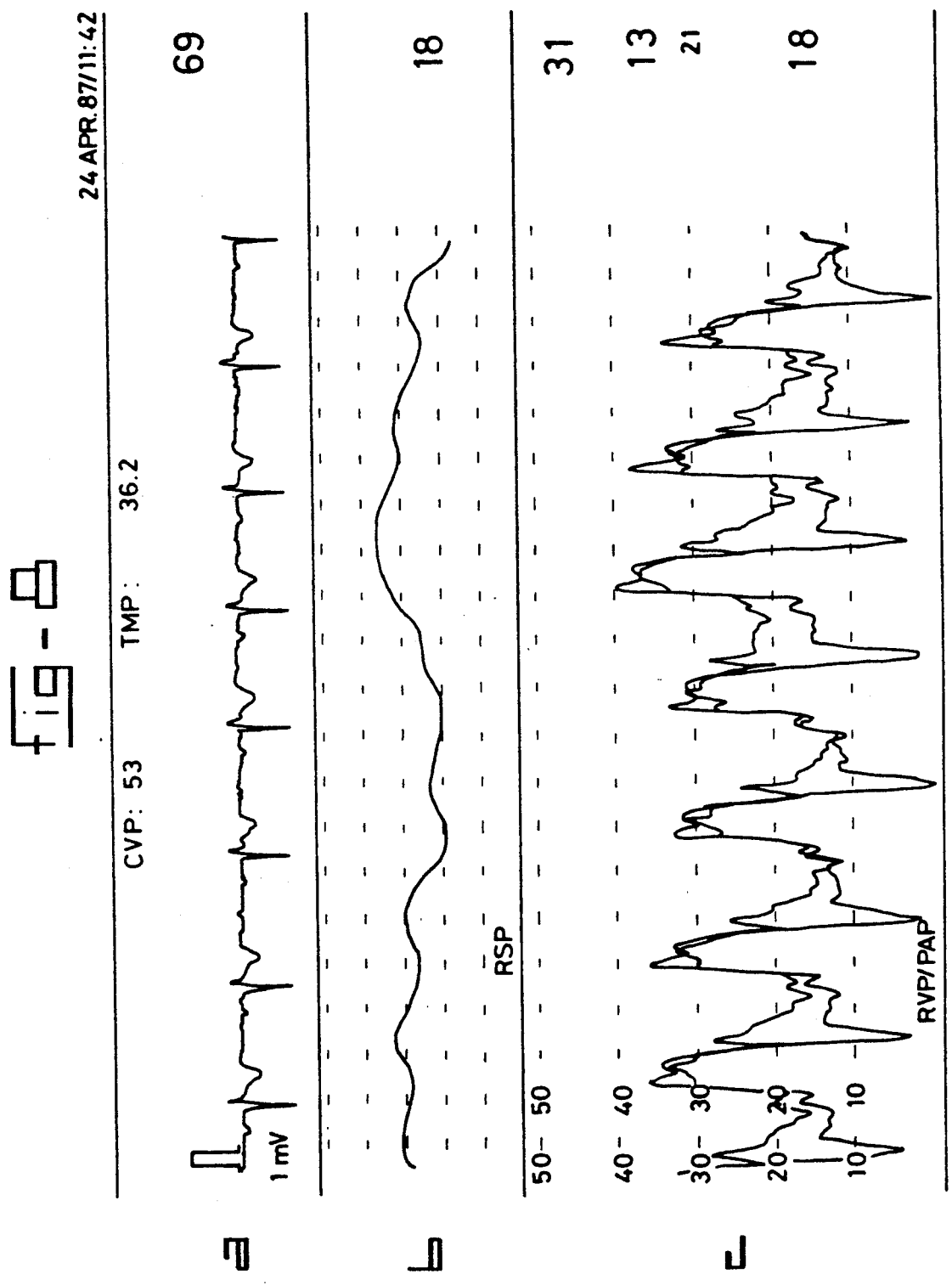

FIG. 8 consecutively shows for a patient: the electrocadiogram (FIG. 8a), the respiration (FIG. 8b) and the simultaneously measured right ventricular pressure (RVP: bottom curve) and pulmonary pressure (PAP: top curve) (FIG. 8c). The two curves in FIG. 8c are measured by the proximal measuring lumen and distal measuring lumen of the catheter according to the invention.

As indicated in FIGS. 7 and 8, the pressure on one side and on the other side of the tricuspid valve and the pulmonary valve can be measured and recorded simultaneously via the proximal and distal measuring lumina during insertion or removal of the catheter. This makes it possible to diagnose stenosis or valvular insufficiency.

The good quality of the pulmonary pressure measurement described above moreover results in the following.

Figure 9:
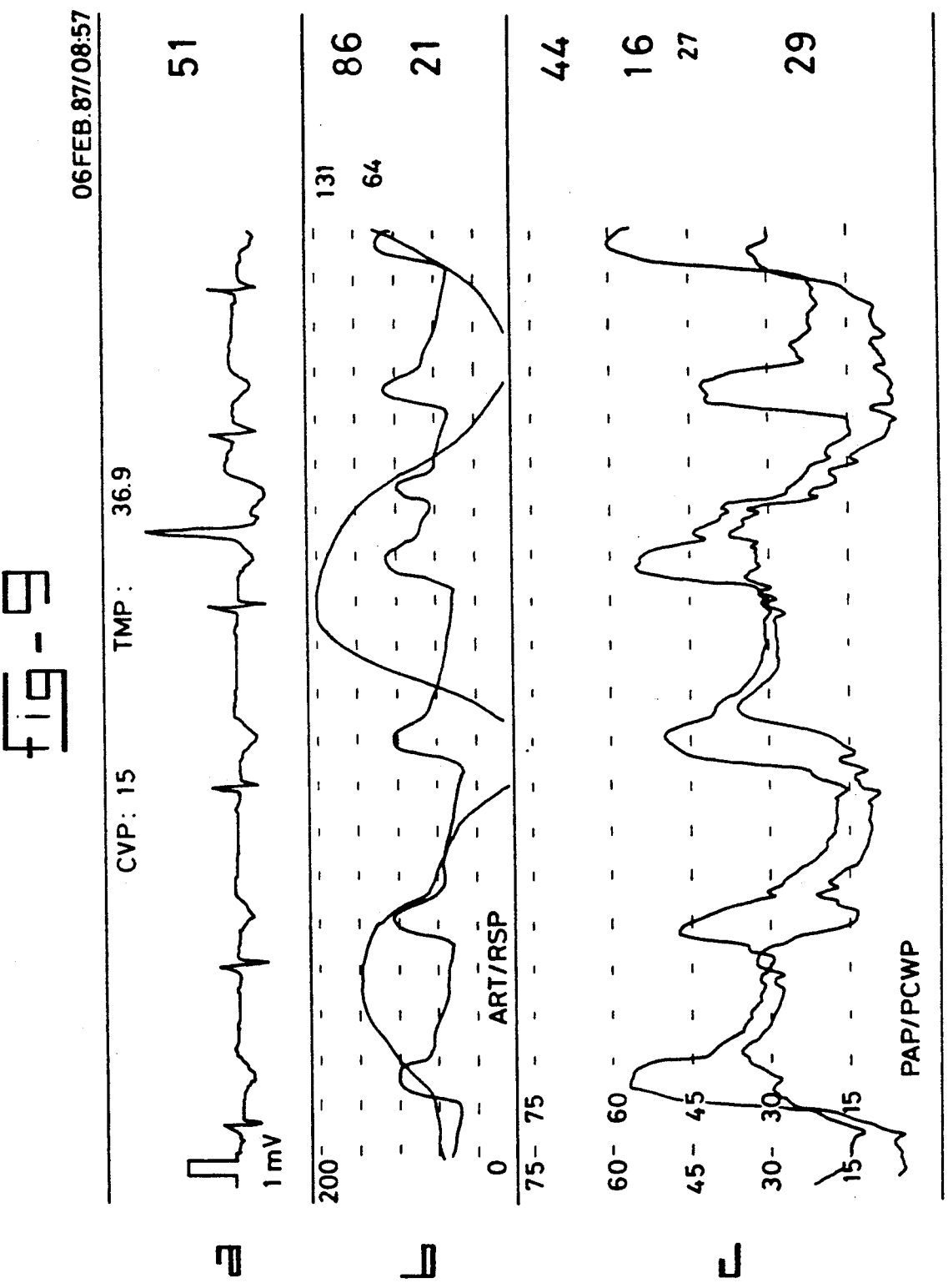
FIGS. 9 and 10 show a few other curves measured according to the invention.

As has been illustrated, the measurement becomes independent of interfering cardiac and respiratory influences due to the simultaneous recording to the PAP curve and the PCWP curve. The intrathoracic pressure changes and hemodynamic fluctuations are completely parallel in the two curves. As an example reference is made to FIG. 9 which shows an interfering cardiac influence (FIG. 9a), i.e. a ventricular extrasystole, and an interfering respiratory influence (FIG. 9b), while said PAP and PCWP curves (FIG. 9c) relative to each other are nevertheless satisfactorily interpretable.

This is also of great importance for calculating the pulmonary vascular resistance (PVR). When measurement of the PAP and PCWP is not carried out in an exact and synchronous manner this may incorrectly result in a negative deflection of the PVR. Unphysiological data may be quickly obtained especially when relying exclusively on digital reading on the monitor and when the fundamental curves are not used for quality control.

PVR is determined using the equation $PVR = \overline{(PAP - LAP)}/CO$, wherein LAP is the left atrial pressure and CO the cardiac output. This cardiac output CO is measured via the known thermodilution method, and for this the catheter is provided with a thermistor. The left atrial pressure (LAP) can be replaced, as indicated in the introduction, approximately by the pulmonary capillary wedge pressure (PCWP).

In the context of analyzing the pulmonary vascular resistance, determined by a viscosity factor to be measured and a vascular factor not to be measured, correct measurement of PCWP and calculation of PVR is of fundamental value for specifying the medical indication. Reduction of iatrogenic complications is a further safety aspect which is not unimportant.

Figure 10:
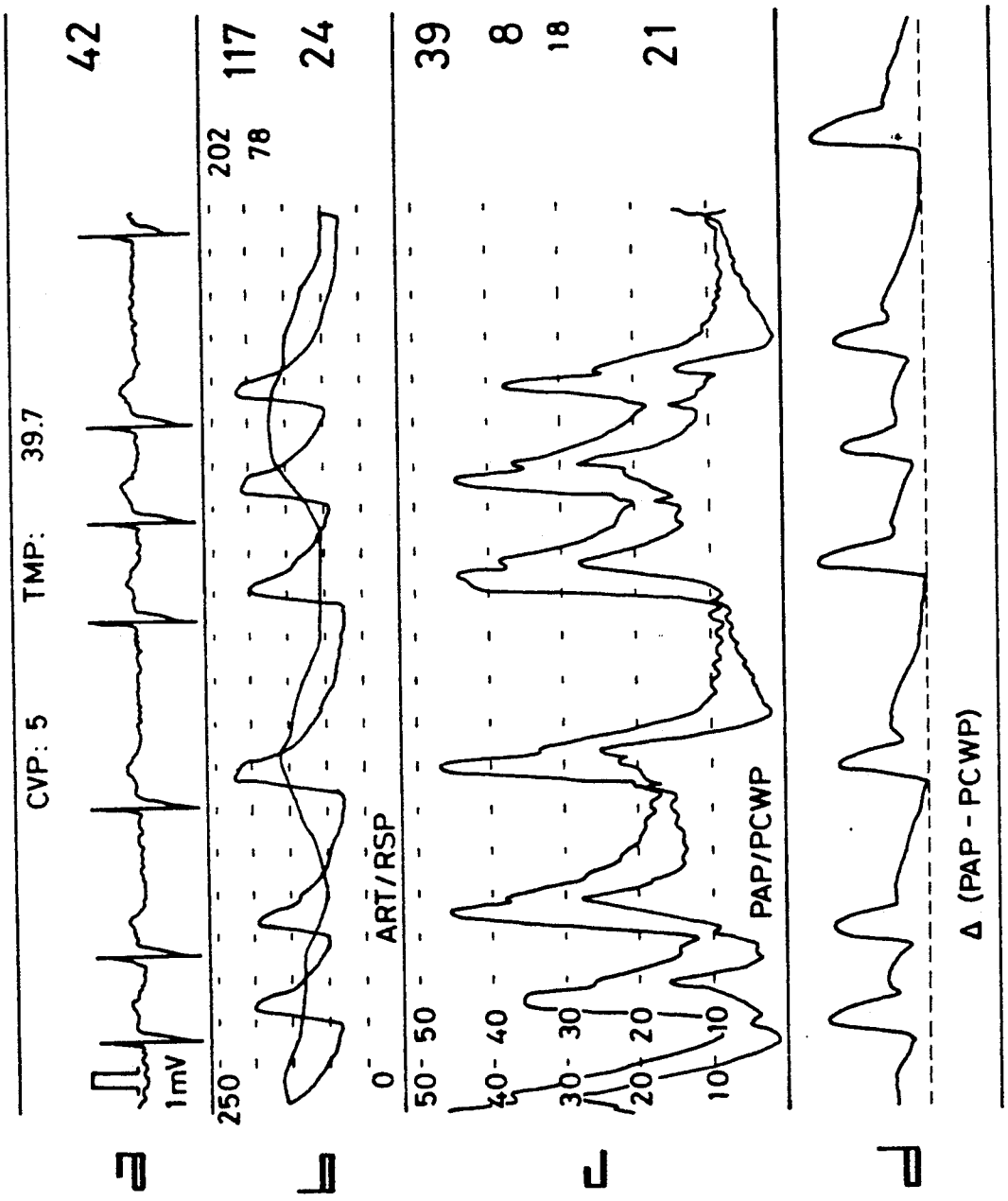

If the PAP curve and the PCWP curve are subtracted from each other as shown in FIG. 10d, a "Δ(PAP−PCWP)" curve can be seen which is completely independent of the respiration (FIG. 10b) and therefore independent of the intrathoracic pressure changes (FIG. 10c) due to respiration, and which is representative of the cardiac output and the pulmonary vascular resistance (CO×PVR).

One of the reasons why pulmonary pressures are difficult to read is that the distal tip of the catheter sometimes "sways" ("catheter-whip effect") and that no satisfactory PAP curve can be distinguished. When the balloon is inflated with preservation of the PAP and PCWP measurements, the distal tip of the catheter is fixed and this problem is largely solved. The possibility of PAP measurement with inflated balloon is lost in the classical catheter.

We claim:

1. Method for carrying out hemodynamic measurements on a patient, using a flow-directed balloon catheter, which is connected to a control and pressure-measuring unit and is at least provided with a distal measuring lumen and a balloon-inflating lumen, comprising the steps of inserting the catheter by way of a suitable vein until the distal end is positioned inside the thorax, subsequently inflating the balloon, inserting the catheter further by way of the right atrium and ventricle into the pulmonary artery until the distal end with the inflated balloon in wedge position is stuck in a branch thereof and closes off the latter, providing a proximal measuring lumen spaced closely to the distal measuring lumen, measuring the pulmonary arterial pressure (PAP) during insertion of the catheter into the pulmonary artery as long as the catheter has not yet arrived in the wedge position via both the proximal measuring lumen and the distal measuring lumen, and simultaneously recording the two relevant, virtually identical pressure curves with the measuring unit.

2. Method for carrying out hemodynamic measurements on a patient using a flow-directed balloon catheter which is connected to a control and pressure-measuring unit and is at least provided with a distal measuring lumen, a balloon-inflating lumen and a proximal measuring lumen spaced closely to the distal measuring lumen, said method comprising the steps of:

inserting the catheter by way of a suitable vein until the distal end is positioned inside the thorax;
subsequently inflating the balloon;
inserting the catheter further by way of the right atrium and ventricle into the pulmonary artery until the distal end with the inflated balloon in wedge position is stuck in a branch thereof and closes off said branch;
measuring pulmonary arterial pressure (PAP) during insertion of the catheter into the pulmonary artery as long as the catheter has not yet arrived in the wedge position via both the proximal measuring lumen and the distal measuring lumen;

measuring, in the wedge position of the catheter with the balloon inflated, the pulmonary arterial pressure (PAP) and the pulmonary capillary wedge pressure (PCWP) via the proximal measuring lumen and via the distal measuring lumen; and simultaneously recording two relevant pressure curves with the measuring unit reflecting said measurement via the proximal measuring lumen and via the distal measuring lumen at all times so that the moment at which the catheter arrives in the wedge position can be clearly detected as said two curves diverge, whereby simultaneous measurement of said pressures relative to each other is independent of interfering cardiac and respiratory influences.

3. Method for carrying out hemodynamic measurements on a patient using a flow-directed balloon catheter which is connected to a control and pressure-measuring unit and is at least provided with a distal measuring lumen, a balloon-inflating lumen and a proximal measuring lumen spaced closely to the distal measuring lumen, said method comprising the steps of:

inserting the catheter by way of a suitable vein until the distal end positioned inside the thorax;

subsequently inflating the balloon;

inserting the catheter further by way of the right atrium and ventricle into the pulmonary artery until the distal end with the inflated balloon in wedge position is stuck in a branch thereof and closes off said branch;

measuring pulmonary arterial pressure (PAP) during insertion of the catheter into the pulmonary artery as long as the catheter has not yet arrived in the wedge position via both the proximal measuring lumen and the distal measuring lumen measuring, in the wedge position of the catheter with the balloon inflated, the pulmonary arterial pressure (PAP) and the pulmonary capillary wedge pressure (PCWP) via the proximal measuring lumen and via the distal measuring lumen simultaneously recording two relevant pressure curves with the measuring unit reflecting said measurement of said pulmonary arterial and pulmonary capillary measurement of said pulmonary arterial and pulmonary capillary wedge pressures at all times so that the moment at which the catheter arrives in the wedge position can be clearly detected as said two curves diverge, whereby simultaneous measurement of said pressures relative to each other is independent of interfering cardiac and respiratory influences; and incidentally inflating the balloon in the wedge position of the catheter and measuring said pulmonary arterial and pulmonary capillary wedge pressures simultaneously via the two measuring lumina in the uninflated and inflated state of the balloon so as to produce virtually identical and mutually different pressure curves on the measuring unit as a result of which the wedge position is exactly determined and a reliable measure of the pulmonary arterial and pulmonary capillary wedge pressures is guaranteed.

4. Method according to claim 3, comprising the step of simultaneously measuring the pulmonary arterial pressure (PAP) and pulmonary capillary wedge pressure (PCWP) via the proximal measuring lumen and via the distal measuring lumen in a spontaneously assumed and upward-displaced wedge position of the catheter with the uninflated balloon producing thereby mutually different pressure curves on the measuring unit, as a result of which the moment at which the catheter without inflated balloon spontaneously arrives in an upward-displaced wedge position can be clearly detected due to the two said curves diverging and an alarm can be given.

5. Method according to claim 3 further comprising the step of generating a gradient curve equal to the difference between the pulmonary arterial pressure and the pulmonary wedge capillary pressure and which is completely independent of respiration and independent of intrathoracic pressure changes due to respiration and which is representative of cardiac output and pulmonary vascular resistance, said gradient curve presenting an exact end-diastolic pressure gradient having an important predictive value to a patient's prognosis.

6. Method according to claim 3 further comprising the step of fixing the distal tip of the catheter within the pulmonary artery by inflating the balloon so as to facilitate an improved measurement of the pulmonary artery pressure measured via the proximal measuring lumen through the avoidance of catheter sway or catheter-whip effect.

7. Method according to claim 2 or 3, in which the catheter has a thermistor lumen near the distal end for a thermodilution measurement in order to determine the cardiac output (CO), the pulmonary vascular resistance $PVR = (\overline{PAP} - \overline{LAP})/CO$ being determined (wherein LAP is the left atrial pressure) by $LAP \sim PCWP$, the intra-thoracic pressure changes, cardiac and respiratory fluctuations which may occur during the measurement of PAP and PCWP having no influence.

8. Method for carrying out hemodynamic measurements on a patient using a flow-directed balloon catheter which is connected to a control and pressure-measuring unit and is at least provided with a distal measuring lumen, a balloon-inflating lumen and a proximal measuring lumen spaced closely to the distal measuring lumen, said method comprising the steps of:

inserting the catheter by way of a suitable vein until the distal end is positioned inside the thorax;

subsequently inflating the balloon;

inserting the catheter further by way of the right atrium and ventricle into the pulmonary artery until the distal end with the inflated balloon in wedge position is stuck in a branch thereof and closes off said branch;

measuring pulmonary arterial pressure (PAP) during insertion of the catheter into the pulmonary artery as long as the catheter has not yet arrived in the wedge position via both the proximal measuring lumen and the distal measuring lumen;

simultaneously recording the two relevant, virtually identical pressure curves with the measuring unit;

measuring, during the insertion of the catheter by way of the right atrium and ventricle into the pulmonary artery or during removal of the catheter therefrom the pressure on one side and on the other side of a valve selected from the group consisting of the tricuspid valve, the pulmonary valve and both tricuspid and pulmonary valves, by means of the proximal and distal measuring lumina and recording the pressure gradient over the said valve on the measuring unit by means of two pressure curves.

* * * * *